(12) United States Patent
Hoshina et al.

(10) Patent No.: US 11,269,087 B2
(45) Date of Patent: Mar. 8, 2022

(54) RADIATION IMAGING APPARATUS AND RADIATION IMAGING SYSTEM

(71) Applicant: CANON KABUSHIKI KAISHA, Tokyo (JP)

(72) Inventors: Tomohiro Hoshina, Kawasaki (JP); Takamasa Ishii, Honjo (JP); Kota Nishibe, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/996,624

(22) Filed: Aug. 18, 2020

(65) Prior Publication Data

US 2020/0379130 A1 Dec. 3, 2020

Related U.S. Application Data

(63) Continuation of application No. PCT/JP2019/006454, filed on Feb. 21, 2019.

(30) Foreign Application Priority Data

Mar. 1, 2018 (JP) .............................. JP2018-036569

(51) Int. Cl.
*G01T 1/20* (2006.01)

(52) U.S. Cl.
CPC .......... *G01T 1/2002* (2013.01); *G01T 1/2006* (2013.01)

(58) Field of Classification Search
CPC ... G01T 1/2002; G01T 1/2006; G01T 1/2018; A61B 6/00
See application file for complete search history.

(56) References Cited

U.S. PATENT DOCUMENTS

| 5,132,539 A * | 7/1992 | Kwasnick | G01T 1/2018 250/361 R |
| 2003/0001100 A1 * | 1/2003 | Dejule | G01T 1/2018 250/370.11 |
| 2003/0127600 A1 * | 7/2003 | Vafi | H01L 31/02322 250/370.11 |

(Continued)

FOREIGN PATENT DOCUMENTS

| JP | H05-242841 A | 9/1993 |
| JP | 2000-009845 A | 1/2000 |
| JP | 2000-284053 A | 10/2000 |

(Continued)

*Primary Examiner* — Kiho Kim

(74) *Attorney, Agent, or Firm* — Canon U.S.A., Inc. I.P. Division

(57) ABSTRACT

A scintillator panel including a scintillator layer that converts incident radiation into light and a scintillator base that supports the scintillator layer, a sensor panel including a sensor substrate that is disposed on a side of the scintillator layer that is opposite to the scintillator base and has a photoelectric conversion portion that converts the light into an electric signal, and a sensor base that is disposed on the side of the sensor substrate that is opposite to the scintillator layer and supports the sensor substrate, and a sealing member that seals a gap between the scintillator panel and the sensor panel at an edge of the scintillator panel are comprised. The sensor panel is provided with a convex member for narrowing the gap at a position in a vertical direction to a surface of the sensor panel from the edge of the scintillator panel.

10 Claims, 6 Drawing Sheets

(56) References Cited

U.S. PATENT DOCUMENTS

| | | | | |
|---|---|---|---|---|
| 2012/0132825 A1* | 5/2012 | Amitani | ................ | A61B 6/542 |
| | | | | 250/394 |
| 2014/0091225 A1* | 4/2014 | Sasaki | .................... | G01T 1/202 |
| | | | | 250/366 |

FOREIGN PATENT DOCUMENTS

| | | | |
|---|---|---|---|
| JP | 2004-335580 A | 11/2004 | |
| JP | 2012-002700 A | 1/2012 | |
| WO | 2001-051951 A | 7/2001 | |

* cited by examiner

RADIATION IMAGING APPARATUS AND RADIATION IMAGING SYSTEM

CROSS-REFERENCE TO RELATED APPLICATIONS

This application is a Continuation of International Patent Application No. PCT/JP2019/006454, filed Feb. 21, 2019, which claims the benefit of Japanese Patent Application No. 2018-036569, filed Mar. 1, 2018, both of which are hereby incorporated by reference herein in their entirety.

BACKGROUND OF THE INVENTION

Field of the Invention

The present invention relates to a radiation imaging apparatus and a radiation imaging system that perform imaging by using radiation.

Background Art

A radiation imaging apparatus developed in recent years includes a sensor panel equipped with multiple photoelectric conversion portions and a scintillator panel, which converts incident radiation such as X-ray into light having a wavelength detectable by the photoelectric conversion portions, stacked (disposed) on the sensor panel.

For example, Japanese Patent Laid-Open No. 2000-009845 discloses a sealing technique for such a radiation imaging apparatus, in which when a scintillator panel and a sensor panel is adhered together, the periphery of these panels is sealed with a resin (sealing member).

For example, in the case in which highly hygroscopic cesium iodide (CsI) is used as a scintillator for the scintillator panel, the sealing member for the radiation imaging apparatus requires a high level of moisture-proofing or moisture-resisting performance. In addition, the larger the area of the sealing member in contact with the outside air, the worse the moisture-proofing or moisture-resisting performance may be.

Japanese Patent Laid-Open No. 2000-009845 does not take into account the moisture-proofing or moisture-resisting performance of the sealing member and is insufficient in the moisture-proofing or moisture-resisting performance of the radiation imaging apparatus.

The present invention is made with such circumstances, and an aspect of the present invention provides a mechanism for improving the moisture-proofing or moisture-resisting performance of the radiation imaging apparatus.

SUMMARY OF THE INVENTION

A radiation imaging apparatus according to the present invention comprises: a scintillator panel including a scintillator layer that converts incident radiation into light and a first base that supports the scintillator layer; a sensor panel including a sensor substrate that is disposed on a side of the scintillator layer that is opposite to the first base and has a photoelectric conversion portion that converts the light into an electric signal, and a second base that is disposed on the side of the sensor substrate that is opposite to the scintillator layer and supports the sensor substrate; and a sealing member that seals a gap between the scintillator panel and the sensor panel at an edge of the scintillator panel, wherein the sensor panel is provided with a convex member for narrowing the gap at a position in a vertical direction to a surface of the sensor panel from the edge of the scintillator panel.

The present invention also covers a radiation imaging system that includes the above radiation imaging apparatus.

Further features of the present invention will become apparent from the following description of exemplary embodiments with reference to the attached drawings.

DESCRIPTION OF THE EMBODIMENTS

Aspects (embodiments) of the present invention will be described with reference to the drawings.

Figure 1A:
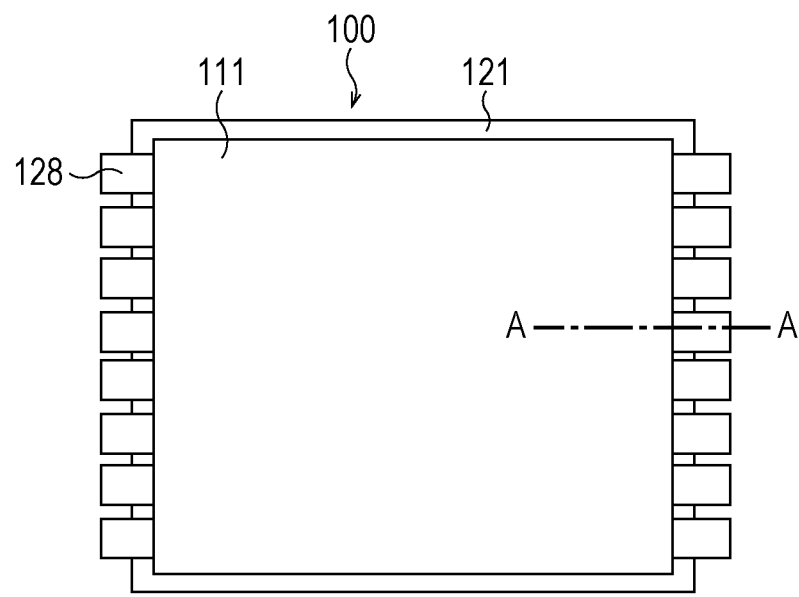
FIG. 1A is a view schematically illustrating a first configuration example of a radiation imaging apparatus according to an embodiment of the present invention.
Figure 1B:
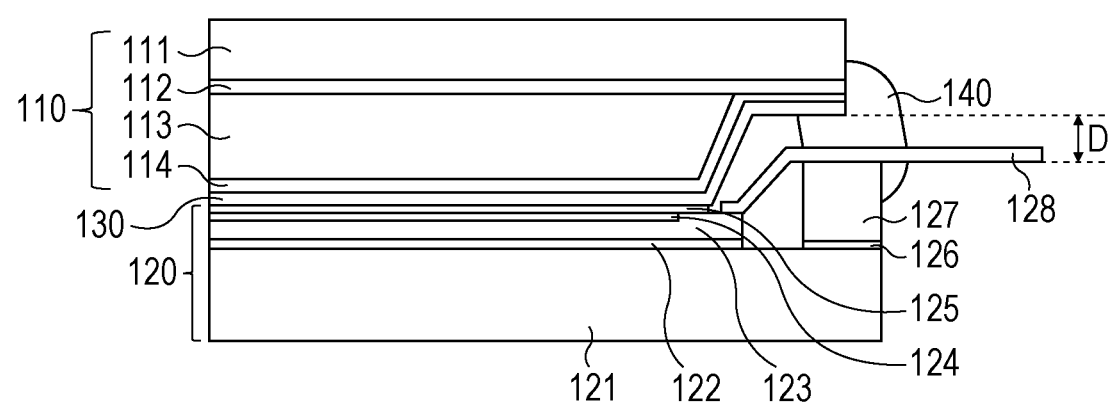
FIG. 1B is a view schematically illustrating the first configuration example of the radiation imaging apparatus according to the embodiment of the present invention.

FIGS. 1A and 1B is a view schematically illustrating a first configuration example of a radiation imaging apparatus 100 according to an embodiment of the present invention. A radiation imaging apparatus applicable to a medical diagnostic imaging apparatus, an analyzer, or the like, is preferred as the radiation imaging apparatus 100, but the present invention is not limited to these apparatuses. Although a type of radiation to be used for imaging of the radiation imaging apparatus 100 is preferably X-rays for example, the present invention is not limited to these X-rays and other types of radiation, such as alpha rays, beta rays, and gamma rays, are also applicable.

Specifically, FIG. 1A is a plan view schematically illustrating the radiation imaging apparatus 100. Also, FIG. 1B is a cross section of the radiation imaging apparatus 100 taken along line A-A in FIG. 1A. In FIGS. 1A and 1B, like elements are denoted by like reference signs.

As illustrated in FIG. 1B, the radiation imaging apparatus 100 according to the present embodiment is configured to include a scintillator panel (fluorescent plate) 110, a sensor panel (a photosensor or a photoelectric conversion panel) 120, a bonding layer 130, and a sealing member 140.

The scintillator panel 110 is configured to include a scintillator base 111, a base-protection layer 112, a scintillator layer 113, and a scintillator-protection layer 114.

The scintillator base 111 is a base (first base) for supporting the scintillator layer 113. This scintillator base 111 is made of a material having a high radiation (X-ray) transmittance. For example, the scintillator base 111 is preferably made of a carbon material (a-C, CFRP) or glass. Also, a reflective layer for facilitating effective use of light converted from radiation in the scintillator layer 113 may be disposed on the scintillator base 111. For example, such a reflective layer may be made of a material, such as silver (Ag) or aluminum (Al), having a high reflectance.

The base-protection layer 112, which is a layer for protecting the scintillator base 111, is disposed between the scintillator base 111 and the scintillator layer 113.

The scintillator layer 113 converts incident radiation into light. Here, the light converted in the scintillator layer 113 may include visible rays and infrared rays. Also, in an example illustrated in FIG. 1B, the scintillator layer 113 is formed with an area smaller than the area of the scintillator base 111. Also, for example, the scintillator layer 113 is made of a columnar crystal scintillator typified by CsI:Tl or cesium iodide slightly doped with thallium (Tl), or made of a granular scintillator typified by GOS:Tb or gadolinium oxysulfide slightly doped with terbium (Tb). In the present embodiment, for example, the scintillator layer 113 is made of the columnar crystal scintillator containing cesium iodide as a main ingredient.

The scintillator-protection layer 114, which is a protection layer for protecting the scintillator layer 113, is disposed between the scintillator layer 113 and the bonding layer 130. For example, the scintillator-protection layer 114 has a function of protecting the scintillator layer 113 from deterioration caused by moisture (moisture-proofing or moisture-resisting function). Especially in the case of the scintillator layer 113 being made of a columnar crystal scintillator, such as CsI:Tl, the scintillator-protection layer 114 is necessary because characteristics of the scintillator layer 113 deteriorate due to moisture degradation. For example, a typical organic material, such as a silicone resin, an acrylic resin, or an epoxy resin, or may be a hot-melt resin, such as a polyester resin, a polyolefin resin, or a polyamide resin may be used as a material of the scintillator-protection layer 114. For example, the scintillator-protection layer 114 may be made of a resin having a low moisture permeability, such as an organic layer of poly-para-xylylene formed by chemical vapor deposition, or a hot-melt resin typified by a polyolefin resin. More specifically, this scintillator-protection layer 114 has a protective function against moisture so as to prevent moisture from entering the scintillator layer 113 from outside and also has a protective function against shock so as to prevent breakage of the scintillator layer 113. For example, in the case of the scintillator layer 113 being made of the scintillator having a columnar crystal structure, the scintillator-protection layer 114 has a thickness of 10 µm to 200 µm. This is because if the thickness of the scintillator-protection layer 114 is less than 10 µm, it is difficult to completely cover the surface of the scintillator layer 113 that has surface undulations and large protrusions due to abnormal growth during vapor deposition, which may lead to deterioration of the protective function against moisture. Meanwhile, if the thickness of the scintillator-protection layer 114 exceeds 200 µm, the light converted in the scintillator layer 113 (or the light reflected by the reflective layer described above) is scattered more in the scintillator-protection layer 114, which may lead to a deterioration in resolution and in MTF (Modulation Transfer Function) for radiation images provided by the radiation imaging apparatus 100.

The sensor panel 120 is configured to include a sensor base 121, a bonding layer 122, a sensor substrate 123 having a photoelectric conversion portion 124, a sensor-protection layer 125, a bonding layer 126, a convex member 127, and an external wire 128.

The sensor base 121 is a base (second base) for supporting the sensor substrate 123, which is disposed on a side of the sensor substrate 123 that is opposite to the side of the scintillator layer 113. The sensor base 121 is preferably made, for example, of a carbon material such as CFRP or amorphous carbon or of glass.

The bonding layer 122 is a bonding layer (second bonding layer) for bonding the sensor base 121 and the sensor substrate 123 together.

The sensor substrate 123 is a substrate disposed on a side of the scintillator layer 113 that is opposite to the side of the scintillator base 111 and having the photoelectric conversion portion 124 for converting the light converted in the scintillator layer 113 into electric signals. The sensor substrate 123 is. This sensor substrate 123 is adhered to the sensor base 121 with the bonding layer 122 interposed therebetween, and, for example, is an insulating substrate made of a material, such as glass. Also, the photoelectric conversion portion 124 in which a photoelectric conversion element (not illustrated) and a switching element (not illustrated), such as a TFT, are arranged two-dimensionally is provided at the sensor substrate 123. The sensor substrate 123 may be a type of which one sheet of the sensor substrate 123 forms one imaging field or a type of which multiple sheets of the sensor substrate 123 form one imaging field. CMOS sensors using crystalline silicon or PIN sensors or MIS sensors using amorphous silicon can be used as a type of the photoelectric conversion elements in the photoelectric conversion portion 124.

The sensor-protection layer 125, which is a layer for protecting the sensor substrate 123, is disposed between the sensor substrate 123 and the bonding layer 130. More specifically, the sensor-protection layer 125 is disposed so as to cover and protect the photoelectric conversion portion 124 of the sensor substrate 123. For example, the sensor-protection layer 125 is preferably made of SiN, $TiO_2$, LiF, $Al_2O_3$, or MgO. Alternatively, the sensor-protection layer 125 may be made, for example, of a polyphenylene sulfide resin, a fluororesin, a polyether ether ketone resin, a liquid crystal polymer, a polyether nitrile resin, a polysulfone resin, a polyether sulfone resin, or a polyarylate resin. Alternatively, the sensor-protection layer 125 may be made, for example, of a polyamide-imide resin, a polyether-imide resin, a polyimide resin, an epoxy resin, or a silicon resin. Note that the sensor-protection layer 125 is preferably made of a material having a high transmittance of light with such wave lengths as converted in the scintillator layer 113 because the light converted by the scintillator layer 113 passes through the sensor-protection layer 125 when radiation is incident on the radiation imaging apparatus 100.

The bonding layer 126 is a bonding layer (third bonding layer) for bonding the sensor base 121 (a surface of the sensor base 121) and the convex member 127 together. This bonding layer 126 preferably has a small thickness in order to improve the moisture-proofing or moisture-resisting performance. In addition, although, in the example illustrated in FIG. 1B, the bonding layer 126 is separated from the bonding layer 122 or the sensor substrate 123, the bonding layer 126 may be formed so as to be in contact with the bonding layer 122 or in contact with a side surface of the sensor substrate 123. For example, the bonding layer 126 may be made of a resin that have a low moisture permeability or a sheet material that have a low moisture permeability. In this case, for example, a typical organic material, such as a silicone resin, an acrylic resin, or an epoxy resin, or a hot-melt resin, such as a polyester resin, a polyolefin resin, or a polyamide resin may be used as the material of the bonding layer 126.

As illustrated in FIG. 1B, the convex member 127 is a peripheral member disposed at a position in a vertical direction to a surface of the sensor panel 120 (more specifically, on a surface of the sensor base 121) from the edge of the scintillator panel 110 (scintillator base 111), and for narrowing a gap between the scintillator panel 110 and the sensor panel 120, and the gap is to be sealed by the sealing member 140, which will be described later. Also, a surface of the convex member 127 on a side of the scintillator panel 110 is closer to the surface of the scintillator base 111 on which the scintillator layer 113 is supported than to a surface of the sensor panel 120 where the convex member 127 is not formed. For example, this convex member 127 is preferably made of a material having a low moisture permeability. For example, this convex member 127 may be formed using a material formed by a resin material, or formed using a carbon material or glass. Note that in order to improve the moisture-proofing or moisture-resisting performance, the convex member 127 is preferably made of a material having a coefficient of thermal expansion close to that of the sensor base 121 or made of the same material as that of the sensor base 121.

The external wire 128 is a wire disposed between the convex member 127 and the scintillator panel 110 and connected to the sensor substrate 123. More specifically, the external wire 128 is wire that couples the sensor substrate 123 electrically to an external flexible board or the like. A bonding pad may be provided at the contact points between the external wire 128 and the sensor substrate 123.

As illustrated in FIG. 1B, the bonding layer 130 is a bonding layer (first bonding layer) for bonding the scintillator panel 110 and the sensor panel 120 together at a position different from the edge of the scintillator panel 110 (the scintillator base 111). More specifically, the bonding layer 130 bonds the scintillator panel 110 and the sensor panel 120 together in such a manner that the scintillator-protection layer 114 of the scintillator panel 110 and the sensor-protection layer 125 of the sensor panel 120 are opposed and adhered to each other. Similarly to the sensor-protection layer 125, the bonding layer 130 is preferably made of a material having a high transmittance of light with wave lengths converted in the scintillator layer 113.

The sealing member 140 is a member for sealing the gap between the scintillator panel 110 and the sensor panel 120 at the edge of the scintillator panel 110 (scintillator base 111). This sealing member 140 conducts sealing that is spaced from the scintillator panel 113 and fixes the convex member 127 to the edge of the scintillator panel 110 (scintillator base 111). In order to improve the moisture-proofing or moisture-resisting performance of the scintillator panel 110, this sealing member 140 may be preferably made by a resin having a low moisture permeability, especially an epoxy resin, as is the scintillator-protection layer 114 or the bonding layer 126. The sealing member 140 may be made of the same material as that of the bonding layer 126. Also, the external wire 128 illustrated in FIG. 1B is sealed by the sealing member 140 so as to pass through the sealing member 140.

To improve the moisture-proofing or moisture-resisting performance of the radiation imaging apparatus 100, the edge of the scintillator panel 110 (scintillator base 111) preferably comes to a position inside the width of the upper surface of the convex member 127 as illustrated in FIG. 1B. Also, when D is a gap (distance) necessary to be sealed by the sealing member 140, $t_a$ is a total thickness of the scintillator layer 113 and the scintillator-protection layer 114, $t_b$ is a thickness of the bonding layer 130, $t_c$ is a thickness of the bonding layer 122, and $t_d$ is a thickness of the external wire 128, the radiation imaging apparatus 100 according to the present embodiment preferably satisfies the formula (1) below.

$$t_b+t_c+t_d \leq D < t_a+t_b \qquad (1)$$

Here, the left side of the formula (1) takes into account the gap that is wider than a thickness of members that may deform during bonding (the gap to prevent the convex member 127 from abutting the scintillator base 111). The right side of the formula (1) takes into account the gap in a condition that the height of the convex member 127 is greater than the height of the sensor-protection layer 125 of the sensor panel 120. In this case, it is more preferable that the gap (distance) necessary to be sealed by the sealing member 140 be closer to the value in the left side of the formula (1) from a view point of improving the moisture-proofing or moisture-resisting performance because the area of the sealing member 140 coming into contact with the outside air can be reduced.

FIG. 2 is a plan view schematically illustrating examples of the positional relationship between the sensor base 121 and the convex member 127 of FIGS. 1A and 1B according to the embodiment of the present invention.

Figure 2A:
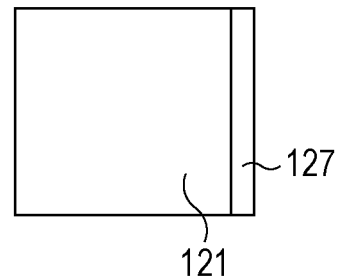
FIG. 2A is a plan view schematically illustrating an example of a positional relationship between a sensor base and a convex member of FIGS. 1A and 1B according to the embodiment of the present invention.
Figure 2B:
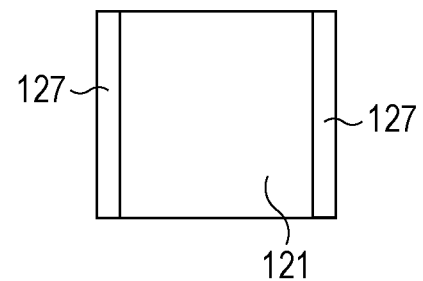
FIG. 2B is a plan view schematically illustrating another example of the positional relationship between the sensor base and the convex member of FIGS. 1A and 1B according to the embodiment of the present invention.
Figure 2C:
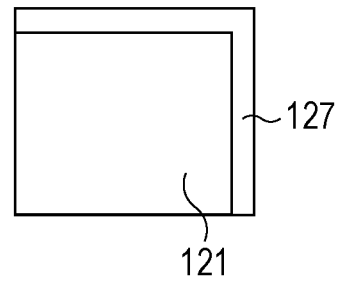
FIG. 2C is a plan view schematically illustrating another example of the positional relationship between the sensor base and the convex member of FIGS. 1A and 1B according to the embodiment of the present invention.
Figure 2D:
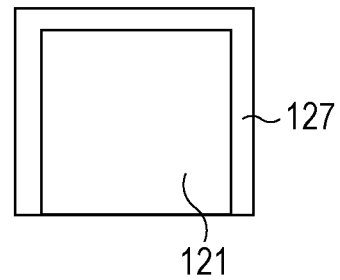
FIG. 2D is a plan view schematically illustrating another example of the positional relationship between the sensor base and the convex member of FIGS. 1A and 1B according to the embodiment of the present invention.
Figure 2E:
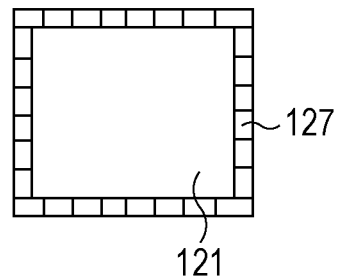
FIG. 2E is a plan view schematically illustrating another example of the positional relationship between the sensor base and the convex member of FIGS. 1A and 1B according to the embodiment of the present invention.
Figure 2F:
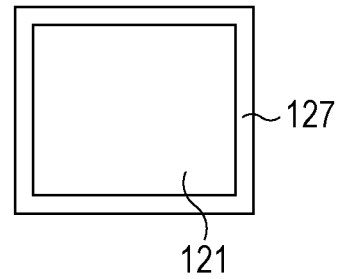
FIG. 2F is a plan view schematically illustrating another example of the positional relationship between the sensor base and the convex member of FIGS. 1A and 1B according to the embodiment of the present invention.

FIG. 2A illustrates a configuration in which the convex member 127 (as well as the bonding layer 126) is disposed along only one side of the sensor base 121. Also, FIGS. 2B and 2C illustrate configurations in which the convex member 127 (as well as the bonding layer 126) is disposed along two sides of the sensor base 121. Also, FIG. 2D illustrates a configuration in which the convex member 127 (as well as the bonding layer 126) is disposed along three sides of the sensor base 121. Also, FIG. 2E illustrates a configuration in which the convex member 127 (as well as the bonding layer 126) is disposed partially along sides of the sensor base 121. Also, FIG. 2F illustrates a configuration in which the convex member 127 (as well as the bonding layer 126) is disposed along all of the four sides of the sensor base 121 (in other words, disposed along the periphery of the sensor base 121 so as to surround the sensor base 121). From a viewpoint of further improving the moisture-proofing or moisture-resisting performance, it is more preferable that the convex member 127 be disposed so as to surround the periphery of the sensor base 121 as illustrated in FIG. 2F.

Figure 3:
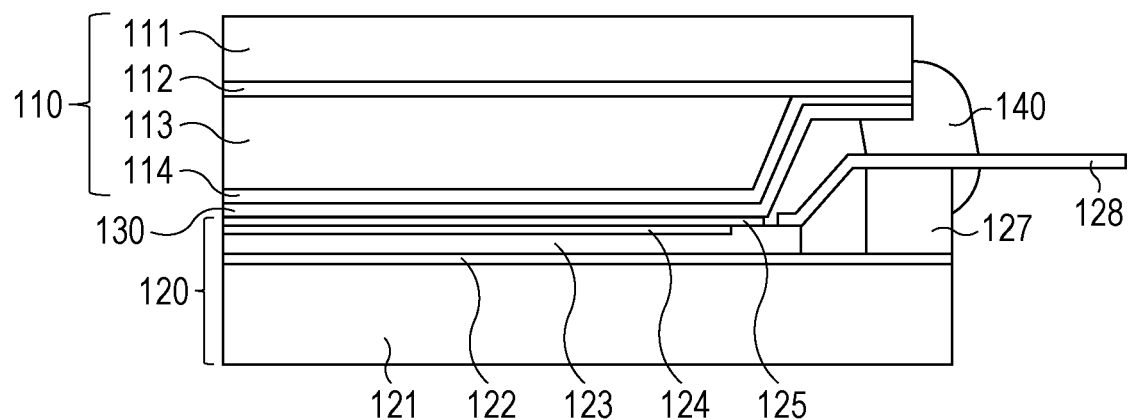
FIG. 3 is a view schematically illustrating a second configuration example of a radiation imaging apparatus according to the embodiment of the present invention.

FIG. 3 is a view schematically illustrating a second configuration example of the radiation imaging apparatus 100 according to the embodiment of the present invention. In FIG. 3, elements similar to those in FIGS. 1A and 1B and in FIG. 2 are denoted by the same reference signs, and detailed descriptions of them will be omitted.

The second example illustrated in FIG. 3 is a configuration in which the bonding layer 126 is included in the bonding layer 122, thereby forming the bonding layer 122 and the bonding layer 126 integrally, compared with the first example illustrated in FIG. 1B. The second example illustrated in FIG. 3 is preferable, for example, in the case of the bonding layer 122 being made of a material having better moisture barrier properties.

Figure 4:
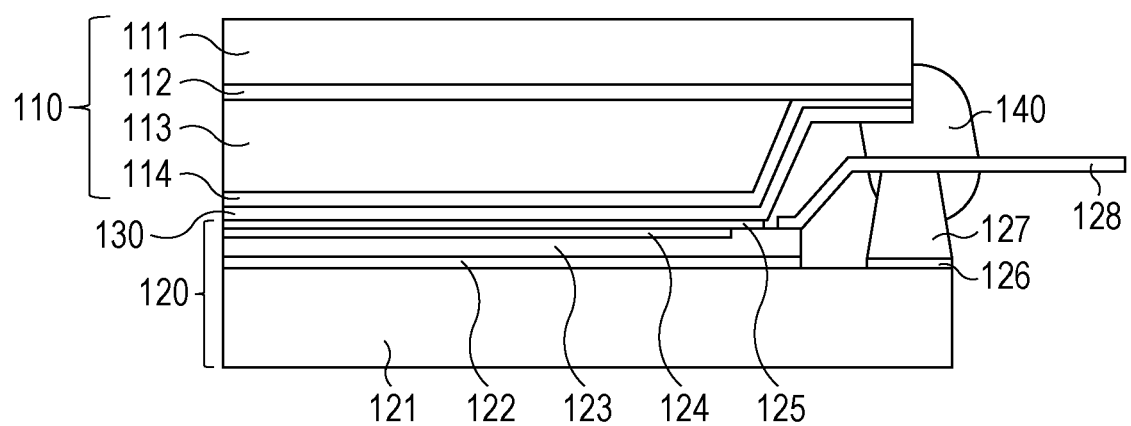
FIG. 4 is a view schematically illustrating a third configuration example of a radiation imaging apparatus according to the embodiment of the present invention.

FIG. 4 is a view schematically illustrating a third configuration example of the radiation imaging apparatus 100 according to the embodiment of the present invention. In FIG. 4, elements similar to those in FIGS. 1A to 3 are denoted by the same reference signs, and detailed descriptions of them will be omitted.

The third example illustrated in FIG. 4 is a configuration in which the shape of the convex member 127 is changed compared with the first example illustrated in FIG. 1B. More specifically, in the third example illustrated in FIG. 4, the convex member 127 is made to have a shape of a trapezoid that is shorter on a side of the scintillator panel 110. The third example illustrated in FIG. 4 is a shape of the convex member 127 that considers, for example, alleviating the stress concentrated on the external wire 128. To alleviate the stress concentrated on the external wire 128, the shape of the convex member 127 may be a shape of a polygon, such as a pentagon or a hexagon.

Figure 5:
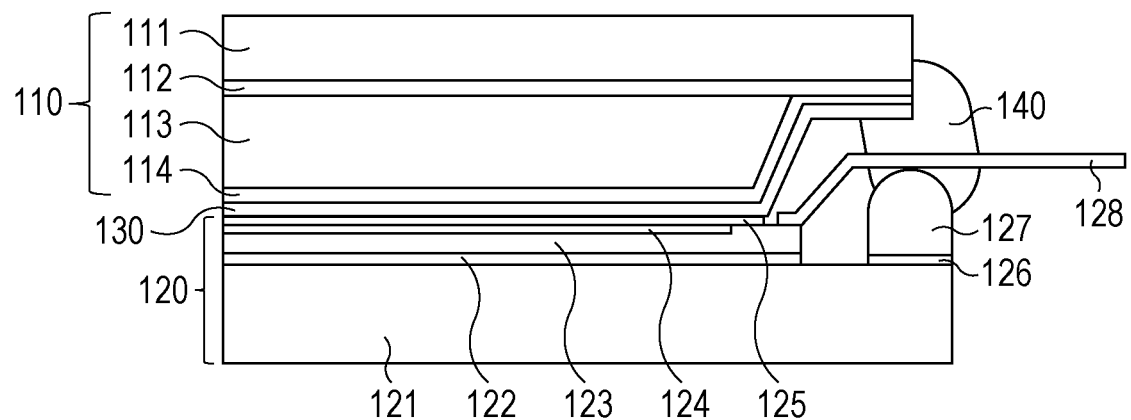
FIG. 5 is a view schematically illustrating a fourth configuration example of a radiation imaging apparatus according to the embodiment of the present invention.

FIG. 5 is a view schematically illustrating a fourth configuration example of the radiation imaging apparatus 100 according to the embodiment of the present invention. In FIG. 5, elements similar to those in FIGS. 1A to 4 are denoted by the same reference signs, and detailed descriptions of them will be omitted.

The fourth example illustrated in FIG. 5 is a configuration in which the shape of convex member 127 is changed compared with the first example illustrated in FIG. 1B. More specifically, in the fourth example illustrated in FIG. 5, the convex member 127 is made with a shape formed with straight lines and a curved line.

Figure 6:
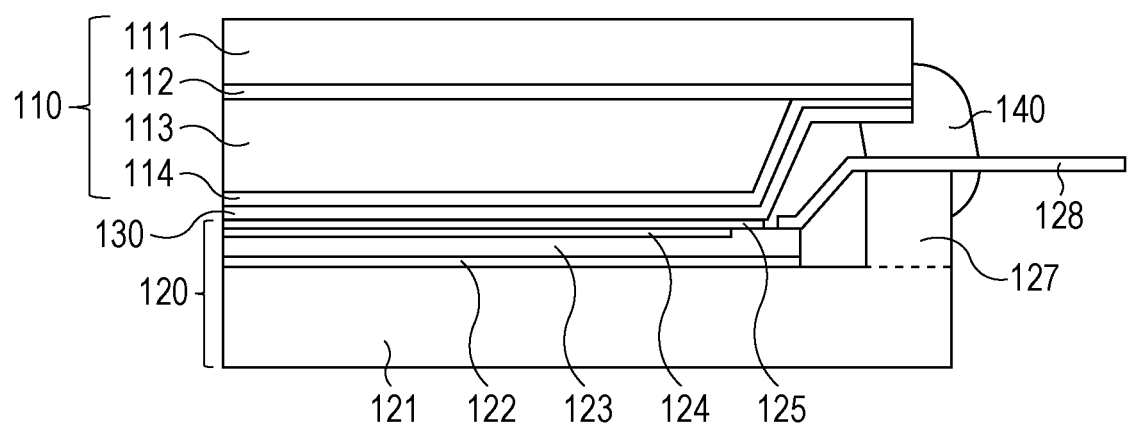
FIG. 6 is a view schematically illustrating a fifth configuration example of a radiation imaging apparatus according to the embodiment of the present invention.

FIG. 6 is a view schematically illustrating a fifth configuration example of the radiation imaging apparatus 100 according to the embodiment of the present invention. In FIG. 6, elements similar to those in FIGS. 1A to 5 are denoted by the same reference signs, and detailed descriptions of them will be omitted.

The fifth example illustrated in FIG. 6 is a configuration in which the convex member 127 is formed integrally with the sensor base 121 compared with the first example illustrated in FIG. 1B. In this configuration, the bonding layer 126 as illustrated in FIG. 1B is not necessary. The fifth example illustrated in FIG. 6 is a preferable configuration for further improving the moisture-proofing or moisture-resisting performance. Note that in the case of the convex member 127 being formed integrally with the sensor base 121 in the fifth example illustrated in FIG. 6, the shape of the convex member 127 may be the trapezoid as illustrated in FIG. 4, the polygon such as the pentagon or the hexagon as described above, or the shape formed by combining straight lines and a curved line as illustrated in FIG. 5.

Figure 7:
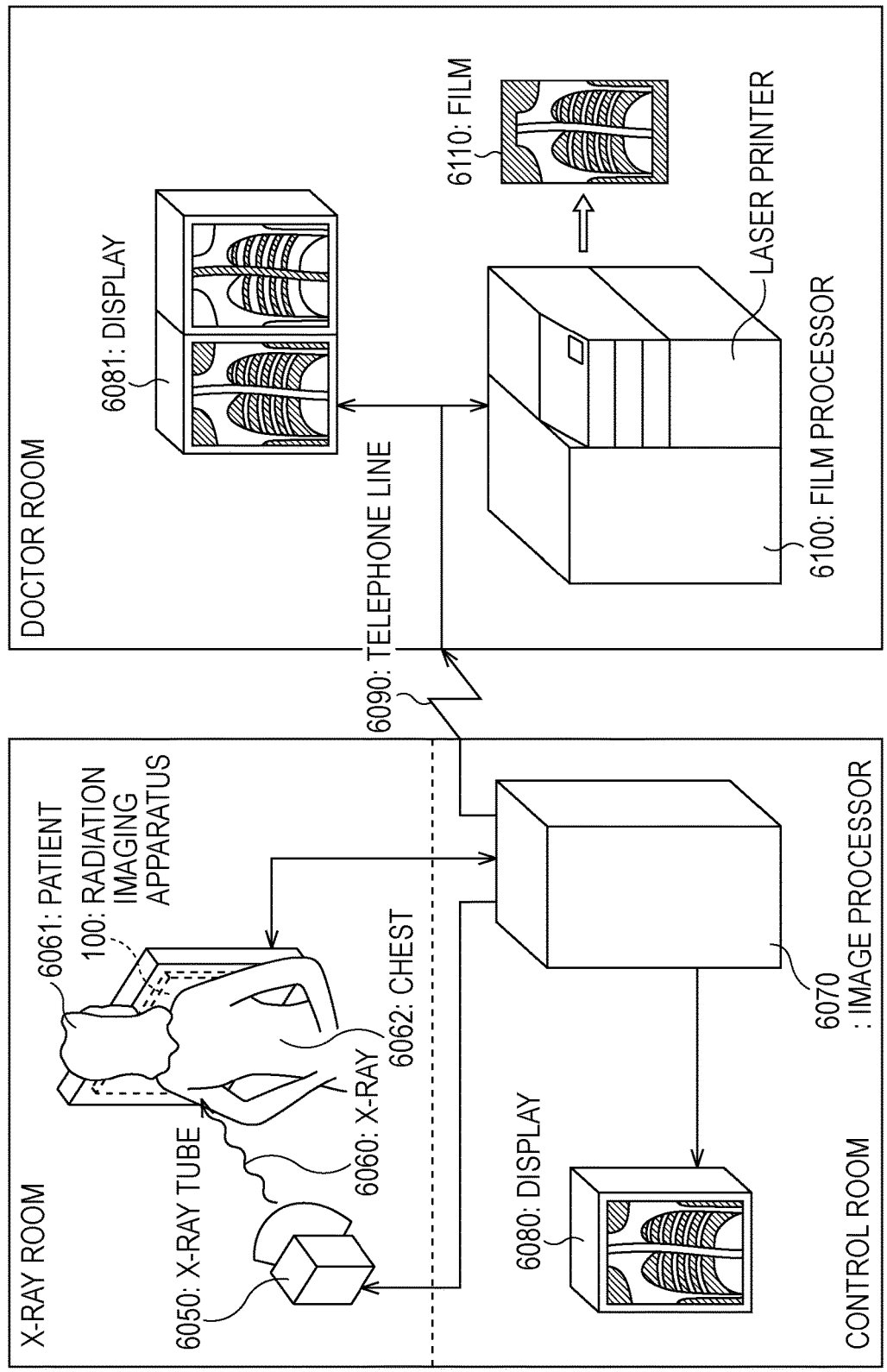
FIG. 7 is a view schematically illustrating a configuration example of a radiation imaging system that includes the radiation imaging apparatus according to the embodiment of the present invention.

FIG. 7 is a view schematically illustrating a configuration example of a radiation imaging system 6000 that includes the radiation imaging apparatus 100 according to the embodiment of the present invention. The radiation imaging apparatus 100 illustrated in FIG. 7 may be any one of the radiation imaging apparatuses illustrated in FIGS. 1A to 6.

The radiation imaging system 6000 illustrated in FIG. 7 includes the radiation imaging apparatus 100, an image processor 6070 equipped with a signal processor and other components, a display 6080 serving as a display device, and an X-ray tube 6050 serving as a radiation generating apparatus for generating radiation.

For example, as illustrated in FIG. 7, X-ray 6060 generated by the X-ray tube 6050 in an X-ray room penetrates the chest 6062 of a patient (subject) 6061 and is incident on the radiation imaging apparatus 100. The X-ray incident on the radiation imaging apparatus 100 contains information on the interior of the body of the patient 6061. In the radiation imaging apparatus 100, the scintillator layer 113 scintillates in response to the incident X-ray. The photoelectric conversion portion 124 of the sensor panel 120 detects the scintillation light and produces electrical information. Subsequently, the image processor 6070 (signal processor) converts the electrical information into digital signals, performs image processing, and displays an X-ray image on the display 6080 in a control room. The X-ray image data obtained by the image processor 6070 can be transmitted to a remote place by using transmission devices including a telephone line 6090 and a network, such as a LAN or the Internet. This enables a doctor at a different location to examine the X-ray image displayed on another display 6081 in a doctor room and to diagnose remotely. For example, the X-ray image can be stored on an optical disk or recorded on a medium such as a film 6110 by a film processor 6100.

In the radiation imaging apparatus 100 according to the present embodiment, the convex member 127 for narrowing the gap between the scintillator panel 110 and the sensor panel 120 is disposed at a position in a vertical direction to a surface of the sensor panel 120 (more specifically, for example, on the surface of the sensor base 121) from the edge of the scintillator panel 110.

With this configuration, the area of the sealing member 140 in contact with the outside air can be reduced, which can thereby improve the moisture-proofing or moisture-resisting performance of the radiation imaging apparatus 100. In addition, if, for example, the thixotropic properties of a resin to be used for the sealing member 140 is low and the gap between the scintillator panel 110 and the sensor panel 120 is large, the application thickness of the resin becomes uneven, and the moisture-proofing or moisture-resisting performance may deteriorate at thin resin portions. In the present embodiment, however, the deterioration of the moisture-proofing or moisture-resisting performance can be prevented by reducing the width of the gap.

According to the present invention, the moisture-proofing or moisture-resisting performance of a radiation imaging apparatus can be improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus comprising:
a scintillator panel including a scintillator layer that converts incident radiation into light and a first base that supports the scintillator layer;
a sensor panel including a sensor substrate that is disposed on a side of the scintillator layer that is opposite to the first base and has a photoelectric conversion portion that converts the light into an electric signal, and a second base that is disposed on the side of the sensor substrate that is opposite to the scintillator layer and supports the sensor substrate; and
a sealing member that seals a gap between the scintillator panel and the sensor panel at an edge of the scintillator panel,
wherein the sensor panel is provided with a convex member for narrowing the gap at a position in a vertical direction to a surface of the sensor panel from the edge of the scintillator panel, and
wherein a wire is provided between the convex member and the scintillator panel, the wire being connected to the sensor substrate.

2. The radiation imaging apparatus according to claim 1, wherein the convex member is provided to be adhered to the second base.

3. The radiation imaging apparatus according to claim 1, wherein the convex member is provided integrally with the second base.

4. The radiation imaging apparatus according to claim 1, wherein a surface of the convex member on a side of the scintillator panel is closer to a surface of the first base that supports the scintillator layer than to a surface of the sensor panel where the convex member is not provided.

5. The radiation imaging apparatus according to claim 1, wherein the wire is sealed by the sealing member so as to pass through the sealing member.

6. The radiation imaging apparatus according to claim 1, further comprising:
a first bonding layer that bonds the scintillator panel and the sensor panel together at a position different from the edge of the scintillator panel, wherein
the scintillator panel is configured to further include a scintillator-protection layer for protecting the scintillator layer,
the sensor panel is configured to further include a second bonding layer that bonds the second base and the sensor substrate, and
$t_b + t_c + t_d \leq D < t_a + t_b$, where D is the gap, $t_a$ is a thickness of the scintillator layer and the scintillator-protection layer, $t_b$ is a thickness of the first bonding layer, $t_c$ is a thickness of the second bonding layer, and $t_d$ is a thickness of the wire.

7. The radiation imaging apparatus according to claim 1, wherein the convex member is a shape of a trapezoid whose width is shorter on a side of the scintillator panel.

8. The radiation imaging apparatus according to claim 1, wherein the convex member is disposed to surround a periphery of the second base.

9. The radiation imaging apparatus according to claim 1, wherein the first base is made of a carbon material or glass.

10. A radiation imaging system, comprising:
the radiation imaging apparatus according to claim 1; and
a radiation generating apparatus for generating the radiation.

* * * * *